US010506341B2

(12) United States Patent
Bromwich et al.

(10) Patent No.: US 10,506,341 B2
(45) Date of Patent: Dec. 10, 2019

(54) COMPUTER-IMPLEMENTED METHOD FOR REDUCING CROSSTALK IN A COMPUTER-BASED AUDIOMETER (71) Applicant: SHOEBOX Ltd., Ottawa (CA)

(72) Inventors: Matthew Bromwich, Ottawa (CA); Guy-Vincent Jourdan, Ottawa (CA); Julian Bromwich, Ottawa (CA); Heikki Koivikko, Ottawa (CA)

(73) Assignee: SHOEBOX LTD., Ottawa (CA)

( * ) Notice: Subject to any disclaimer, the term of this patent is extended or adjusted under 35 U.S.C. 154(b) by 0 days.

(21) Appl. No.: 15/768,355

(22) PCT Filed: Oct. 6, 2016

(86) PCT No.: PCT/CA2016/000249
§ 371 (c)(1),
(2) Date: Apr. 13, 2018

(87) PCT Pub. No.: WO2017/063069
PCT Pub. Date: Apr. 20, 2017

(65) Prior Publication Data
US 2018/0317008 A1 Nov. 1, 2018

(30) Foreign Application Priority Data
Oct. 15, 2015 (CA) .................................. 2908891

(51) Int. Cl.
H04R 3/14 (2006.01)
A61B 5/12 (2006.01)
(Continued)

(52) U.S. Cl.
CPC .............. H04R 3/14 (2013.01); A61B 5/121 (2013.01); G10K 11/178 (2013.01); H03G 3/32 (2013.01);
(Continued)

(58) Field of Classification Search
None
See application file for complete search history.

(56) References Cited

U.S. PATENT DOCUMENTS

2013/0156238 A1* 6/2013 Birch ...................... H03F 3/181
381/309

* cited by examiner

Primary Examiner — Curtis A Kuntz
Assistant Examiner — Kenny H Truong
(74) Attorney, Agent, or Firm — Frost Brown Todd LLC (57) ABSTRACT A computer-implemented method for reducing undesired crosstalk signals on an inactive channel of a device comprising the steps of: (i) determining system volume levels and associated signal amplitudes required to achieve a range of desired audio output attenuation levels on an active channel of the device; (ii) determining a crosstalk compensation signal comprising a signal amplitude and associated phase shift required to reduce undesired crosstalk on the inactive channel of the device for each desired audio output attention level in the range of desired audio output attenuation levels; and (iii) generating a desired audio output attenuation level on the active channel of the device by generating a signal at the determined system volume level and associated signal amplitude required to achieve said desired audio output attenuation level, and generating a contemporaneous crosstalk compensation signal on the inactive channel of the device by generating a signal at the determined signal amplitude and associated phase shift required to reduce the undesired crosstalk on the inactive channel.

18 Claims, 11 Drawing Sheets (51) Int. Cl.
*H04R 5/04* (2006.01)
*G10K 11/178* (2006.01)
*H03G 3/32* (2006.01)
*H04B 3/32* (2006.01)
*A61B 5/00* (2006.01)
*H04R 5/033* (2006.01)

(52) U.S. Cl.
CPC ............... *H04B 3/32* (2013.01); *H04R 5/04* (2013.01); *A61B 5/6815* (2013.01); *A61B 5/7275* (2013.01); *A61B 2505/09* (2013.01); *A61B 2560/0223* (2013.01); *A61B 2560/0406* (2013.01); *H04R 5/033* (2013.01); *H04R 2430/01* (2013.01); *H04R 2430/03* (2013.01)

Figure 1

Pseudocode to create an array of samples to pass to the operating system to produce a sine wave

```
for interval = 0; interval < sampleRate; interval++ {
    var time = frequency / sampleRate * interval;
    sample[interval] = amplitude * sin ( 2 * pi * frequency *
        time );
}
```

Pseudocode for generating a phase shift

```
var phase = -1; // 1 means 0 degrees. -1 means 180 degrees.
for interval = 0; interval < sampleRate; interval++ {
    var time = frequency / sampleRate * interval;
    sample[interval] = amplitude * sin ( 2 * pi * frequency *
        time ) * phase;
}
```

Figure 4

Table: Example SystemVolumeLevelTable (SVLT) which maps system volume (0 to 1) to Audio Voltage Attenuation (dB of attenuation).

Note: Greatest voltage output level is at Index=0.

| Index | System Volume Level | Audio Voltage Attenuation (dB) |
|---|---|---|
| 0 | 1.000000 | 0 |
| 1 | 0.986000 | -0.48 |
| 2 | 0.977000 | -1.01 |
| 3 | 0.967000 | -1.49 |
| 4 | 0.958000 | -2.01 |
| 5 | 0.948000 | -2.5 |
| …. | …. | …. |
| x | 0.000000 | -115.45 |

Figure 5

Affect of adjusting System Volume (v) and Signal Amplitude (a) on resulting decibel level

This plots volume response curves of an Apple iPad

Note 1: For the 'a' plot v = 1, and for the 'v' plot a = 1.

Note 2: "Level" means System Volume Level for the 'v' plot, and means Signal Amplitude for the 'a' plot.

Note 3: The 'v+a' plot is simply the sum of the 'v' and 'a' plots to demonstrate that a broad decibel range can only be achieved by controlling both 'v' and 'a'.

Figure 6

Pseudocode to query the system volume level and calculate the signal amplitude for producing a sound at the given target attenuation.

Note: SVLT is an abbreviation for "SystemVolumeLevelTable" from Figure 5.

```
func calculateOutputLevel(targetAttenuation) {
    var index = findSVLTIndex(targetAttenuation);
    /* Calculate how much we need to attenuate the signal by
        in order to achieve the targetAttenuation. */
    signalLevelAttenuation =
        targetAttenuation - SVLT[index].audioVoltageAttenuation;
    amplitude = decibelstoAmplitude(signalLevelAttenuation);
    return { SVLT[index].systemVolumeLevel, amplitude }
} func findSVLTIndex(targetAttenuation) {
    for (index = 1; index < SVLT.size; index ++) {
        if (targetAttenuation > SVLT[index].audioVoltageAttenuation) {
            /* This audioVoltageAttenuation would reduce volume by
            too much so return index -1 (which is less attenuation) */
            return (index - 1);
        }
    }
    return SVLT.size - 1;
}
```

Figure 7

Pseudocode to set the system volume level, and generate the waveform samples at the desired amplitude.

```
system.setVolumeLevel( systemVolumeLevel );
for interval = 0; interval < sampleRate; interval++ {
    var time = frequency / sampleRate * interval
    sample[interval] =
        amplitude * sin(2 * pi * frequency * time)
}
```

Figure 8

Pseudocode to calculate the required crosstalk compensation amplitude for the system volume level being used by the active channel.

```
func calculateCrosstalkAmplitude
    (activeChannelAttenuation, crosstalkAttenuation) {

/* Find system volume's portion of attenuation for active channel */
    var index = findSVLTIndex(activeChannelAttenuation);
    audioVoltageAttenuation = SVLT[index].audioVoltageAttenuation;

/* Find required signal attenuation to achieve crosstalkAttenuation */
    signalLevelAttenuation =
        targetCrosstalkAttenuation - audioVoltageAttenuation;

/* Return required crosstalk amplitude */
    return decibelstoAmplitude(signalLevelAttenuation);
}
```

Figure 9

Note: In systems that we've tested, the bulk of crosstalk is either very near 0 degrees or very near 180 degrees of phase to the active channel. The above visualizes crosstalk manifesting at 180 degrees.

Figure 10

Pseudocode for generating samples for creating a crosstalk compensation signal on the inactive channel.

```
func generateCrosstalkCompensationSamples(
    frequency, activeChannelAttenuation) { struct {amplitude, phase} =
        queryCSAT(frequency, activeChannelAttenuation);

for interval = 0; interval < sampleRate; interval++ {
        var time = frequency / sampleRate * interval;
        crossTalkSample[interval] =
            amplitude * sin(2*pi*frequency*time) * phase;
    } return crossTalkSample;
}
```

Note: The queryCSAT() method above simply maps the 2 input keys to the 2 output values using the CSAT structure. The workings of this implementation-specific function should be obvious to the reader skilled in the arts, so we have not included the details here.

Figure 11

Pseudocode to determine the correct phase to use when generating the crosstalk compensation signal

```
// Initially set the CSAT entry for the current frequency and active  channel
attenuation to have phase = -1 (ie 180 degrees).
setCSATPhase(frequency, activeChannelAttenuation, -1);

// Generate samples for crosstalk compensation
crosstalkSample = generateCrosstalkCompensationSamples(
      frequency, activeChannelAttenuation); // see Figure 11

// While both the active channel and crosstalk signals are playing,
measure the new level of crosstalk.
OutOfPhaseMeasurement = [measure inactive channel on a sound meter]

// Now set the CSAT entry for the current frequency and active  channel
attenuation to have phase = 1 (ie 0 degrees).
setCSATPhase(frequency, activeChannelAttenuation, 1);

// Generate samples for crosstalk compensation
crosstalkSample = generateCrosstalkCompensationSamples(
      frequency, activeChannelAttenuation);

// While both the active channel and crosstalk signals are playing,
measure the new level of crosstalk.
InPhaseMeasurement = [measure inactive channel on a sound meter]

// Return the phase that produces the lowest level of crosstalk.
if (InPhaseMeasurement < OutOfPhaseMeasurement)
      return 1;  // in-phase
else
      return -1; // out-of-phase
```

Figure 12

Crosstalk Signal Adjustment Table (aka "CSAT")

| Keys | | Values | |
|---|---|---|---|
| Frequency | Attenuation | Amplitude | Phase |
| 250 | -48.5 | 0.23 | 1 |
| 250 | -49.8 | 0.19 | 1 |
| ... | ... | ... | ... |
| 500 | -23.7 | 0.46 | -1 |
| 500 | -24.3 | 0.43 | -1 |
| ... | ... | ... | ... |

Note 1: We have illustrated this structure using "Attenuation" as one of the keys. In audiometer applications, it may be more convenient to use "Hearing Level" (HL) as a key instead. As noted in the background information of this disclosure, there is a direct conversion between HL and Attenuation.

Note 2: In the above illustration, we have shown only values of 1 and -1 in the phase column. This is a simplification which allows only storing a phase of 0 or 180 degrees. If required, it is a simple modification to instead store the phase in degrees so that any phase angle could be stored. In that case, the full non-simplified sine-wave generation formula mentioned in the definitions of this disclosure would be used when generating the crosstalk signal.

Note 3: Since crosstalk compensation is specific to each transducer, an instance of the CSAT structure would be required for every transducer that is calibrated, and also for each channel of those transducers.

COMPUTER-IMPLEMENTED METHOD FOR REDUCING CROSSTALK IN A COMPUTER-BASED AUDIOMETER

FIELD OF THE INVENTION

The present invention relates to a method for reducing "crosstalk", the unwanted transmission of signals between communication channels, in an audiometer. In particular, the present invention relates to a computer-implemented method for reducing crosstalk in a computer-based audiometer.

BACKGROUND OF THE INVENTION

Figure 1:
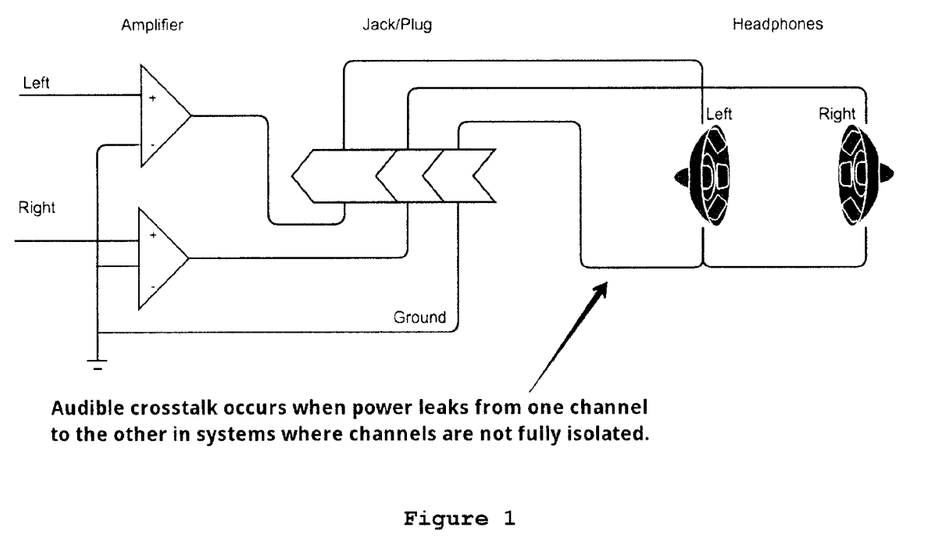
FIG. 1 is a graphical depiction showing crosstalk in a system where channels are not fully isolated.

Crosstalk, the unwanted transmission of signals between communication channels, in the context of hearing testing means that an unwanted audible signal is present on the inactive channel. Crosstalk occurs when power leaks from one channel to the other in systems where channels are not fully isolated (see FIG. 1).

ANSI/ASA S3.6-2010 regulates the maximum allowable levels of crosstalk for a compliant audiometer. According to this standard, crosstalk must either be less than 0 dB HL (which means that is not detectable by an average person with normal hearing) or at least 70 dB SPL quieter than the signal on the active channel.

While purpose-built audiometers meet this standard through the use of hardware designed to electrically isolate the left and right channels, a software audiometer running on a computer or mobile device needs to take extra steps in order to meet the standard. A common approach is to augment the computer or mobile device with external hardware, usually called a DAC, that is custom-designed to generate sound in accordance with the ANSI standard.

The present invention, however, describes methods of implementing a crosstalk-cancellation system entirely through the use of novel software that allows for the use of audio hardware that does not fully isolate the left and right channels. In addition, through the teachings of the present invention, it is also possible to build equivalent external hardware that is designed to remove crosstalk from an audio system using the same basic novel technique as described herein.

SUMMARY OF THE INVENTION

The crosstalk compensation system of the present invention is capable of handling nonlinear or even completely unpredictable crosstalk with a varying signal phase. Purpose-built audiometer hardware doesn't need anti-crosstalk algorithms because the hardware is designed in such a way as to avoid crosstalk. For computer-based audiometers built on a generic platform, such as a PC, Mac, iOS or Android device however, the hardware has typically not been designed to minimize crosstalk to within ANSI standards, which leads to the need for the present software-based crosstalk cancellation technique.

The method of the present invention is not the same as active-noise-cancellation which relies on a feedback loop driven by directly sampling the sound to be cancelled. For generic mobile platforms there is no direct access to sampling the undesired sound so it is necessary to predictively cancel the sound rather than reactively cancel it. Cross-talk shape varies depending on the hardware used (i.e. mobile device, cables and audio connectors, transducers), and varies with changes to either the source signal volume or frequency. There is no single shape for the crosstalk signal that will globally cancel crosstalk. The solution of the present invention therefore relies on calibrating values for each individual configuration.

In one embodiment, the present invention provides a computer-implemented method for reducing an undesired crosstalk signal in an audiometer by software means alone. The software means generally comprises generating a counter signal that is equal in frequency and phase and opposite in amplitude to the undesired crosstalk signal.

In another embodiment, the present invention provides a computer-implemented method for reducing undesired crosstalk signals on an inactive channel of a device comprising the steps of: (i) determining system volume levels and associated signal amplitudes required to achieve a range of desired audio output attenuation levels on an active channel of the device; (ii) determining a crosstalk compensation signal comprising a signal amplitude and associated phase shift required to reduce undesired crosstalk on the inactive channel of the device for each desired audio output attention level in the range of desired audio output attenuation levels; and (iii) generating a desired audio output attenuation level on the active channel of the device by generating a signal at the determined system volume level and associated signal amplitude required to achieve said desired audio output attenuation level, and generating a contemporaneous crosstalk compensation signal on the inactive channel of the device by generating a signal at the determined signal amplitude and associated phase shift required to reduce the undesired crosstalk on the inactive channel.

In yet another embodiment of the present invention, the step of determining system volume levels and associated signal amplitudes required to achieve the range of desired audio output attenuation levels on the active channel of the device comprises the steps of: (i) measuring an output level at each system volume level of the device from maximum level to minimum level when the associated signal amplitude is set at 1; (ii) converting the output level at each such system volume level into decibels of attenuation; (iii) storing the decibels of attenuation for each system volume level in a database; (iv) querying the database to find the system volume level that attenuates the output level to as close to, but not more than, the desired audio output attenuation level; (v) calculating an attenuation required on the signal amplitude, which when added to the decibel of attenuation achieved at said system volume level, will result in producing the desired audio output attenuation level; (vi) storing the calculated attenuation required on the signal amplitude in the database; and (vii) repeating steps (iv) to (vi) for all system volume levels in the database.

In yet a further embodiment of the present invention, the step of determining the crosstalk compensation signal comprising the signal amplitude and associated phase shift required to reduce undesired crosstalk on the inactive channel of the device for each desired audio output attention level in the range of desired audio output attenuation levels comprises the steps of: (i) generating a tone for the desired audio output attenuation level by controlling the system volume level and associated signal amplitude required to generate said tone; (ii) measuring the undesired crosstalk on the inactive channel of the device; (iii) calculating a signal amplitude that would be required to eliminate the undesired crosstalk on the inactive channel without modifying the system volume level; (iv) generating a candidate crosstalk compensation signal at a phase of 180 degrees in accordance with step (iii); (v) re-measuring the undesired crosstalk and iteratively adjusting the associated signal amplitude until the measured undesired crosstalk is minimized; (vi) generating a candidate crosstalk compensation signal at a phase of 0 degrees in accordance with step (iii); (vii) re-measuring the undesired crosstalk and iteratively adjusting the associated signal amplitude until the measured crosstalk is minimized; and (viii) comparing the candidate crosstalk compensation signal at a phase of 180 degrees to the candidate crosstalk compensation signal at a phase of 0 degrees to determine which compensation signal is more effective at reducing the undesired crosstalk, and storing the signal amplitude and phase of such more effective crosstalk cancellation signal in a database.

In yet another embodiment of the present invention, the step of generating the desired audio output attenuation level on the active channel of the device comprises querying the database for the system volume level and associated signal amplitude required to achieve said desired audio output attenuation level, and the step of generating a contemporaneous crosstalk compensation signal on the inactive channel of the device comprises querying the database for the signal amplitude and phase required to achieve said crosstalk compensation signal.

It is important to note that the device used in association with the method of the present invention may be, but is not limited to, a computer-based audiometer having channels that are not fully isolated. There may be other devices having channels that are not fully isolated where it would be useful to reduce or eliminate crosstalk from an inactive channel by means of the method of the present invention.

In another embodiment, the present invention also provides a computer program product comprising a computer readable memory storing computer executable instructions thereon that when executed by a computer with channels that are not fully isolated performs the method steps described above.

DETAILED DESCRIPTION OF THE INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the scope of the invention. Thus, the present invention is not intended to be limited to the embodiments disclosed, but is to be accorded the widest scope consistent with the principles and features disclosed herein.

A crosstalk reduction system and method is disclosed for use in a computer-based audiometer. Crosstalk which couples between channels is reduced through use of a software module which modifies digital samples being sent to a digital-to-analog converter. The following definitions will assist in understanding the nature of the invention as described herein.

Definitions

Audiometer—A machine used for evaluating hearing loss.

Decibel (dB)—Used in audiometry when referring to sound levels. The decibel is a logarithmic unit that expresses the ratio of two values of a physical quantity. It is important to understand, for example, that a change in volume from 20 dB to 30 dB represents 10 times the power level, and a change from 20 dB to 40 dB represents 100 times the power level.

dB SPL—Sound Pressure Level (SPL): The local pressure deviation from the ambient (average, or equilibrium) atmospheric pressure, caused by a sound wave. A sound meter displays the "loudness" of a sound with this unit.

RETSPL Reference Equivalent Threshold Sound Pressure Level. This is the minimum sound level (measured in dB SPL) that a normal person can detect. Audiometers need RETSPL values for each frequency being tested. RETSPL values are specific to each type of headphone and are published for common headphones.

dB HL—Hearing Level (HL). This unit is used to label the "volume control" knob on audiometers, and is also used on the Y-axis of an audiogram to denote the hearing thresholds of the patient. 0 dB HL represents the point at which the human ear can no longer hear the sound. The HL scale is frequency-specific, relates to dB SPL using frequency-specific RETSPL values for the headphones, and has the following relationship: dBHL=dbSPL−RETSPL.

ANSI/ASA S3.6-2010—The most recent specification for audiometers (see: http://webstore.ansi.org/RecordDetail.aspx?sku=ANSI%2FASA+S3.6-2010)

Relationship between RETSPL and dB HL—Unlike sound meters, the human ear is not equally sensitive to all sound frequencies. Thus 0 dB SPL (as read on a sound meter) does not represent "no sound" for a human ear. 0 dB HL is higher than 0 dB SPL but by an amount that varies by frequency. The number of decibels to add to 0 dB SPL to reach 0 dB HL is specific to the headphone used and the frequency. This is the RETSPL value for the frequency. RETSPL=dBSPL−dBHL.

Sine Wave—The sine wave or sinusoid is a mathematical curve that describes a smooth repetitive oscillation and is defined by: a*sin (ωt+phase)=a*sin(2πft+phase) where:
  a=amplitude
  ω=angular frequency=2π*f, where f is frequency
  t=time
  phase=the phase, specifies (in radians) where in its cycle the oscillation is at t=0.

Note that if only phase of 0 or 180 degrees is required, the formula can be simplified to:

$$a*\sin(2\pi ft) \text{ (for phase=0)}$$

or $$a*\sin(2\pi ft)*-1 \text{ (for phase=180)}$$

Active channel—The audio output channel presenting to the ear being tested.

Inactive channel—The audio output channel presenting to the ear that is not being tested (i.e. the channel where crosstalk manifests).

Amplitude (in the domain of sound)—the objective measurement of the degree of change (positive or negative) in atmospheric pressure (the compression and rarefaction of air molecules) caused by sound waves.

Attenuation—The decrease in amplitude of a signal. This is measured in decibels from the initial amplitude to the attenuated amplitude.

Sample—A value at a specific point in time. In the field of audiology this is referring to a calculated value of the sine wave at a given point in time.

Sample Rate—Specifies the frequency of samples to produce a digital audio signal.

System Volume Level—The audio output power level of the system (between 0.0 and 1.0).

Audio Voltage (v)—The measured audio output in voltages.

Audio Voltage Attenuation (dB)—The audio channel voltage converted to attenuation in decibels relative to the maximum output voltage Signal on the active channel—The audio signal of specific frequency and amplitude that is produced on the audio channel that is connected to the patient ear under test.

Crosstalk Signal—The unwanted sound manifesting on the inactive channel.

Crosstalk Cancellation Signal—The produced signal to cancel the crosstalk signal.

Modules/Components

Sample Generator—Produces a stream of digital samples which are sent to a digital-to-analog converter. It is configured with various parameters which affect the characteristics of the output e.g. frequency, amplitude, and phase.

Calibration Parameters Lookup Module—A module, that for a specified frequency and signal attenuation, returns parameters with which the Sample Generator should be configured in order to produce the required output.

Two Channel Digital-to-Analog Converter—A hardware component of the computer-based audiometer which consumes digital data and produces audio output.

Simplifications for Illustrative Purposes

For the purpose of making the method of the present invention more clear, we will remove certain complicating factors that are not part of the core innovation:

1) We will only use dB SPL, not dB HL in algorithms. In the domain of audiometers, the reader who is skilled in the art will recognize that the dB HL unit is easily calculated from the dB SPL value by simply subtracting the RETSPL value for the headphones. For describing how to eliminate crosstalk however, this conversion complicates the description unnecessarily. We will note that it can also be more convenient in an audiometer implementation to use dB HL for indexing into several of the data structures described in this disclosure, and this is an obvious modification that can be made to the data structures that we describe.

2) We will exclude headphone-specific offsets in algorithms. In the domain of sound generation, each headphone of a specific model responds slightly differently to input power, so for audiometers a calibration process is followed to find a compensation factor to "tune" the headphones. We will describe in detail how to find that compensation value for background information, however for algorithm clarity, we will assume this compensation factor is 0 when describing how to compensate for crosstalk. A reader skilled in the art will know that any final output value calculated from the simplified algorithms described in this disclosure will need to be shifted up or down by the "tuning" compensation value specific to each headphone used.

Procedure to Generate a Tone

First, the person skilled in the art will need to become familiar with the procedure to generate a simple sine wave signal at a specified frequency and phase. The basic sine wave (without worrying about phase shift for now) is produced by using the following Sine Wave formula: a*sin (2πft). The frequency (f) and amplitude (a) remain fixed. When digitally generating a sine wave, the time (t) is quantized into intervals called samples. Only the time (t) variable changes for each sample point along the length of the wave. In the above formula, t is replaced by an interval-dependent time by defining time as time=frequency/sample_rate*interval. So, for example, if the frequency is 1 Hz and the sample rate is 30 per second, then 30 samples are needed for 1 second of sound. When finding the 5th (index 4) of the 30 samples (numbered 0 to 29), we would thus set t=1/30*4.

The system of the present invention is designed to use an "audio output framework" typically provided by either the computer's operating system (OS) or a sound generation library. The audio output framework requires a set of samples in an array-like structure and it takes care of producing an audible analogue audio signal from the provided samples. Audio Output Frameworks vary in their methods of requesting and filling the audio sample buffers however. For example, some audio output frameworks poll the application when the sample buffer requires more data, while others rely on the application to actively send new samples on a regular basis. The same system for creating the buffer applies in either case however.

Figure 2:
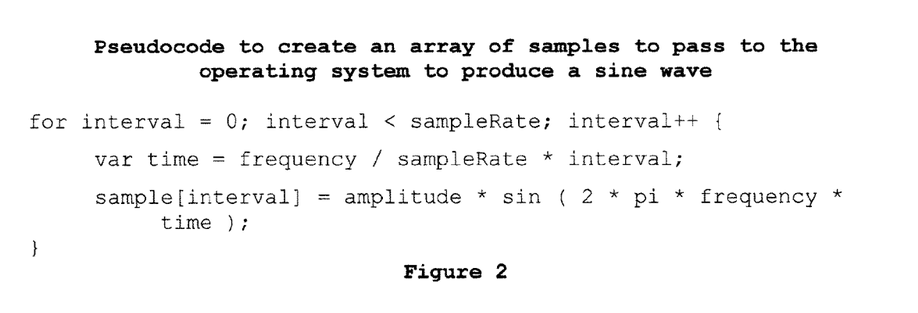
FIG. 2 shows pseudocode to create an array of samples to pass to the operating system to produce a sine wave.

The pseudocode shown at FIG. 2 creates an array of samples to pass to the operating system to produce a sine wave. Variables that control the maximum amplitude and frequency of the waveform are controlled outside of the loop. The loop itself iterates, at a calculated interval (ie. sample rate), over one full sine wave cycle.

Figure 3:
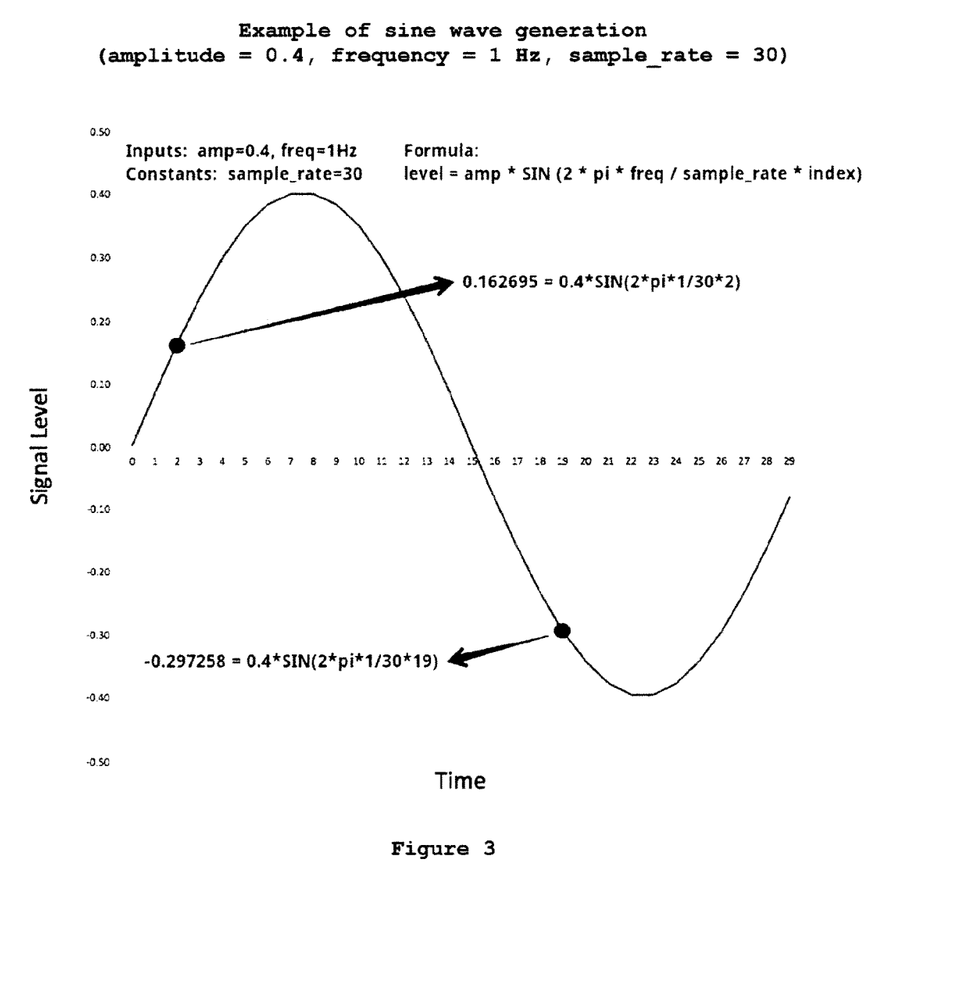
FIG. 3 is a graphical depiction of a sine wave generated by using the algorithm at FIG. 2 when the amplitude is set to 0.4 and the frequency is set to 1 Hz.

If we were to prepare a graph using the algorithm at FIG. 2 (in this case setting the frequency to 1 Hz, the amplitude to 0.4, and the sample rate to 30 per second) the wave as shown at FIG. 3 is generated.

For most applications you would not use a sample rate as low as 30 Hz of course. A digital audio sample rate of 44.1 kHz is more typical and so requires 44100 samples to be calculated for generating 1 second of sound.

Phase Shift

The phase of a sine wave essentially controls the starting point of the wave along the X axis. It is measured by the 360 degrees of a circle. At 180 degrees, the wave appears as the vertical mirror image of the same wave at 0 degrees, in other words it is equal to the 0 degree wave multiplied by −1.

Figure 4:
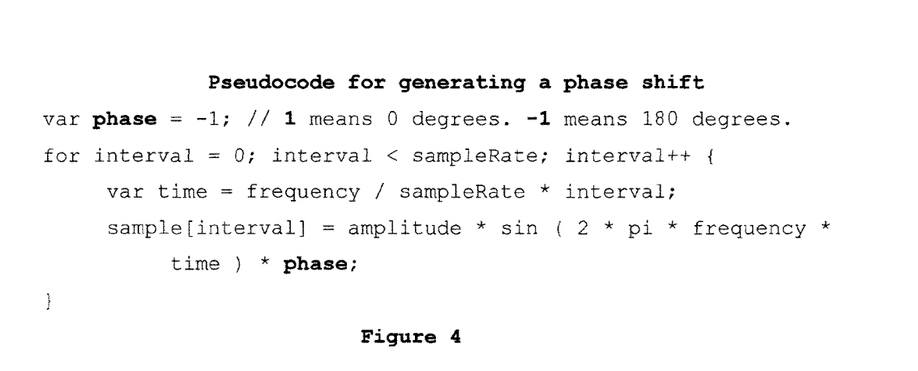
FIG. 4 shows pseudocode for generating a phase shift.

The basic formula for generating a phase shift is a*sin (2πft+phase), but if there is only the need to support a phase shift of 180 degrees, the formula can be simplified to just:

$a*\sin(2\pi ft)$ (for 0 degrees)

or $a*\sin(2\pi ft)*-1$ (for 180 degrees)

as illustrated by the modified pseudocode shown at FIG. 4.

Procedure to Produce an Accurate Volume Level

As a prerequisite to describing the process for eliminating the cross-talk signal on the inactive channel, it is necessary to first describe how the system generates tones in a way that achieves an accurate volume level for each frequency on the Active Channel.

In any programmable computer device capable of generating sound, there are usually two factors which combine to produce the resulting sound. The first factor is the Signal Level—this is the amplitude ('a') of the waveform generated or played by the software. The second factor is the System volume level—this is the hardware "volume control" ('v') of the device which physically amplifies or dampens the signal.

The most straight-forward way to calibrate power output levels is to build a table that maps the desired output level (db SPL) to the required levels of each of the 2 input factors noted above. It is apparent that for any desired sound output level, there are many possible combinations of the two inputs that can produce the desired output level.

The skilled person might consider always leaving the System volume level at 50% and just varying the signal level from e.g. 0% to 100%. However, the problem with this is that the skilled person would likely find that they can't achieve the desired sound range. For instance, at 50% power level, with the signal level at 0%, the ground noise (ie. "hiss") from the amplifier will limit how quiet the output can be, and with the signal level at 100%, the maximum output level will likely not be loud enough to meet requirements. The same type of problems occur with the system volume level permanently set to 0% or 100%.

The skilled person might next consider choosing a handful of System volume levels (e.g. 0%, 20%, 40%, . . . , %100) with various signal levels for each, so that all desired output levels can be reached. This certainly can work, but there's a consequence. The table built for such a method would have Signal Levels increasing for each desired output level until the next System volume level increase is reached, at which point the signal level would start back at a lower value than the previous one. This means that the signal value increases non-linearly across the volume range. For example, if the 35 dB and 36 dB straddled a System volume level step, the signal level could be higher for 35 dB than for 36 dB. Although this could work perfectly well to produce the right output level, it is not recommended because this will make crosstalk cancellation more complex since system volume level adjustment (a physical characteristic of the hardware) is inherently nonlinear and does not follow a calculable trajectory.

Instead, it is best to start with the Signal Level at maximum (amplitude=1) for the whole volume range, and to then choose the System volume level which produces a sound slightly louder than the target SPL. Once at that system volume level, the signal level is then adjusted downward (i.e. "attenuated") by the smallest amount possible until the desired sound level is reached. While it is true that the signal amplitude will therefore vary throughout the output volume range, it has been found that this method results in the most even and predictable steps, and makes cross-talk compensation easier to handle.

Process of Building a Table for the System Volume Levels

When using typical consumer hardware, the exact affect of adjusting the system volume level is not known ahead of time.

In order to have a method of producing accurate volume levels, we need to first create a mapping of decibel levels to system volume levels. Since decibels are a measure of 10× change, there is no way to describe the change if starting at 0. Instead we must describe the change in decibels relative to the loudest possible output and work downwards. Everything is always based from the maximum possible output, which is why the table we will build starts from the maximum output and works downwards.

To find the loudest possible voltage output, we produce a sign wave at amplitude=1 (ie. maximum height) and set the system volume=1 (ie. maximum power). Without the headphones connected, using a voltage meter (or oscilloscope) connected to the audio output jack, while leaving the signal amplitude at 0, we incrementally turn down the volume level and record the resulting voltage change (see formula below), all the way to the lowest system volume level.

Convert the voltage reading into decibels with this formula:

$$dB = 20 \times \text{Log}(test\_voltage/maximum\_voltage)$$

Example: If the maximum voltage the system can output is 2.0 Volts when System Power=1.0, then if a System Power of 0.985 is applied and you measure it as 1.87 Volts, you would record Audio Voltage Attenuation=20×Log (1.87/2.0)=−0.58 dB for a System Volume Level of 0.985.

When using systems that present the volume control API as a floating point number between 0.0 and 1.0, it is necessary to first quantize this range into a countable set. This can be done by experimentally incrementing through the range from 0.0 to 1.0 at some resolution (e.g. by 0.00001 steps) and looking for any measurable changes in the output to determine how many significant digits are really available in the API.

Figure 5:
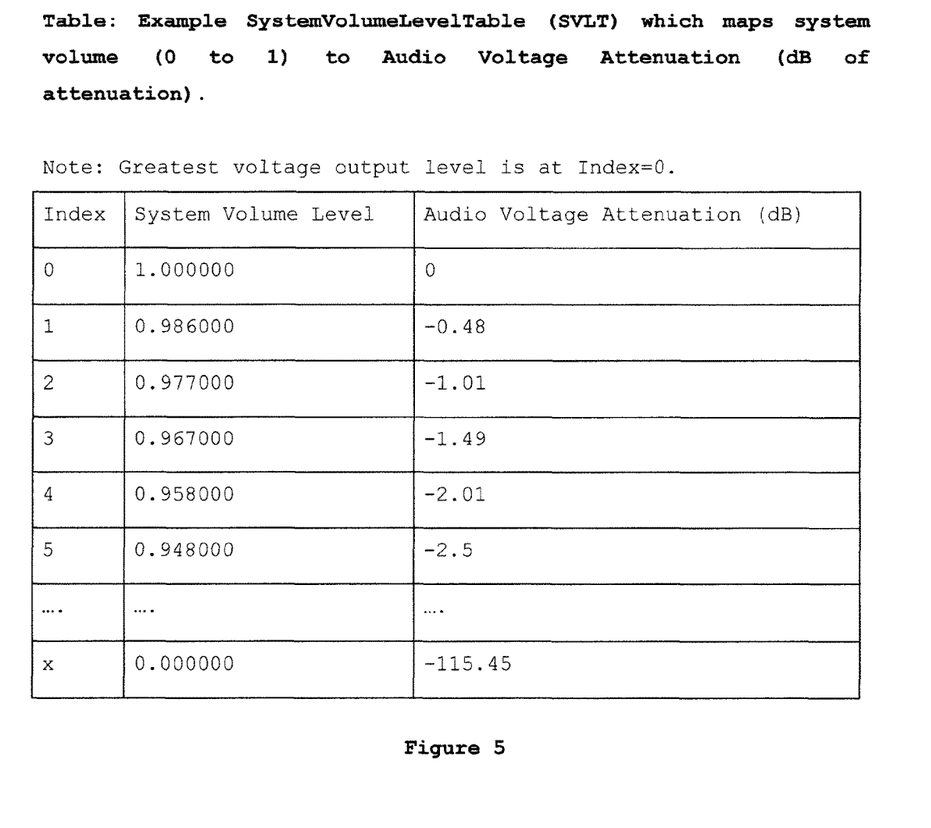
FIG. 5 is an example System Volume Level Table (aka "SVLT") containing the mapping of System Volume Level to Audio Voltage Attenuation.

In the example shown in FIG. 5, the values were measured using a software oscilloscope running on a laptop. The measurement was conducted by changing the system volume level (controlled in this case by a floating point number between 0 and 1) in small increments starting from the maximum (1.000000), and working downwards to the minimum (0.000000) while maintaining the signal amplitude at 100%. The result of the measurement is a table mapping System Volume Level to Audio Voltage Attenuation, which we'll call "SystemVolumeLevelTable" (or SVLT for short). The Audio Voltage Attenuation is measured in dB and is a measure of the change in voltage from the maximum possible output.

By using SystemVolumeLevelTable, the application now has the information needed to produce a signal that is, for example, 2.01 dB below the device maximum output level by setting the system volume to 0.958000 along with a signal amplitude of 1 (the amplitude range is from 0 to 1).

It is important to note that the table at FIG. 5 is still referring to how the system volume control affects the output voltage level. The next step is of course to attach headphones to see how loud (dB SPL) the sound is at maximum power output. The maximum dB SPL is of course headphone dependent (and measuring that maximum dB SPL is the essence of headphone calibration), but with good audiometric headphones that respond linearly to voltage change, regardless of their particular maximum output level, the sound level will attenuate from that maximum level precisely according to the values in the Audio Voltage Attenuation column of the SVLT when the signal amplitude is set to 1.

The table at FIG. 5 therefore allows us to have the information necessary to produce sound at any chosen decibel level, but only for the values listed in the table. To get more resolution between those values and more range at the quiet end, it is also necessary to combine system volume control with attenuating the signal (ie. reducing the amplitude below 1).

Figure 6:
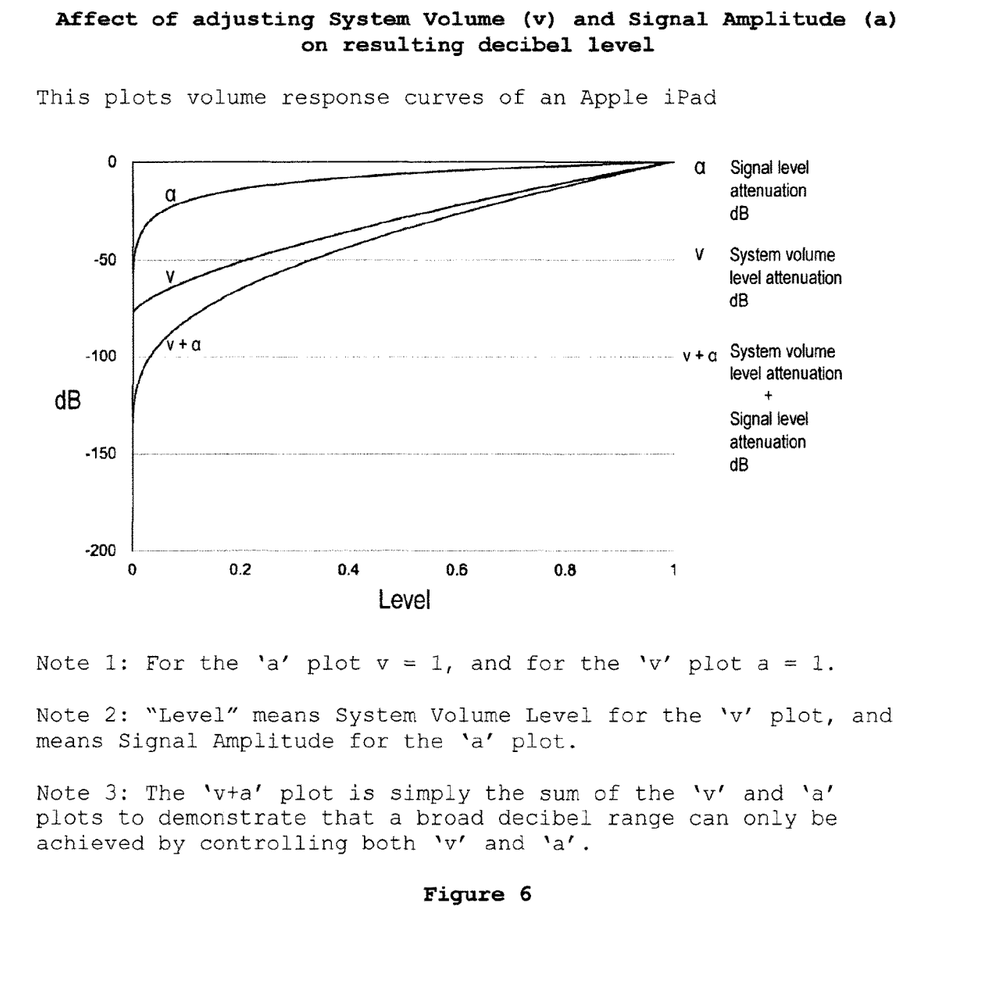
FIG. 6 is a graphical depiction of the effects of adjusting power level and signal level on the resulting decibel level.

The graph at FIG. 6 illustrates how, in isolation, neither the system volume level attenuation nor signal level attenuation would provide enough range, but when combining them together will allow the application to achieve a high signal to noise ratio (ie. avoiding "speaker hiss") over a large range.

It is important to observe that the "v+a" line has the largest decibel range of the 3 lines. It can therefore produce very quiet sounds (bottom-left), while still being able to produce very loud sounds (top-right).

Process of Adjusting the Signal Level

When a target attenuation value is requested by the user, the application needs to determine the required system volume level and also the required signal attenuation.

To simplify the explanation below, we will assume that the user's input is provided simply as an attenuation (dB). For example if they want to produce 70 dB HL on headphones with a RETSPL of 8 dB (for the chosen frequency) on headphones that can maximally produce say 123 dB SPL, we'll assume they've already converted this to an overall required attenuation of −45 dB (−45=(70+8)−123). So we just need to attenuate our maximum signal by −45 dB in this case.

To find the required System Volume Level, we iterate through the SVLT table (as shown at FIG. 5) to find the Audio Voltage Attenuation value that would attenuate the output as much as possible, but not more than the target attenuation. Once the corresponding System Volume Level has been read from the table, we must calculate how much more attenuation is still required to achieve the Target Attenuation.

For example, if the target attenuation is −45 dB, the application would use the lookup table to find the lowest system volume level attenuation value which is bigger than the target attenuation. Using the table at FIG. 5 we might find a System Volume Level that achieves exactly −44.00 dB of Audio Voltage Attenuation. Therefore we must attenuate the signal by another −1.0 dB to reach the target. ie. (−1.0)=(−45)−(−44)

This formula is thus simple:

Signal attenuation (dB)=Target Attenuation (dB)−Audio Voltage Attenuation (dB)

The required Signal Attenuation then needs to be converted from decibels into Amplitude in order for us to use this value to adjust the sine wave (which has an amplitude value between 0 and The following well-known formula does this conversion:

Amplitude=10^(Decibels/20)

We can wrap this in a convenient function as follows:

```
func decibelstoAmplitude(dB) {
    return pow(10, dB/20)
}
```

Continuing with the above example, −1.0 dB therefore converts to a signal Amplitude of 0.891.

Figure 7:
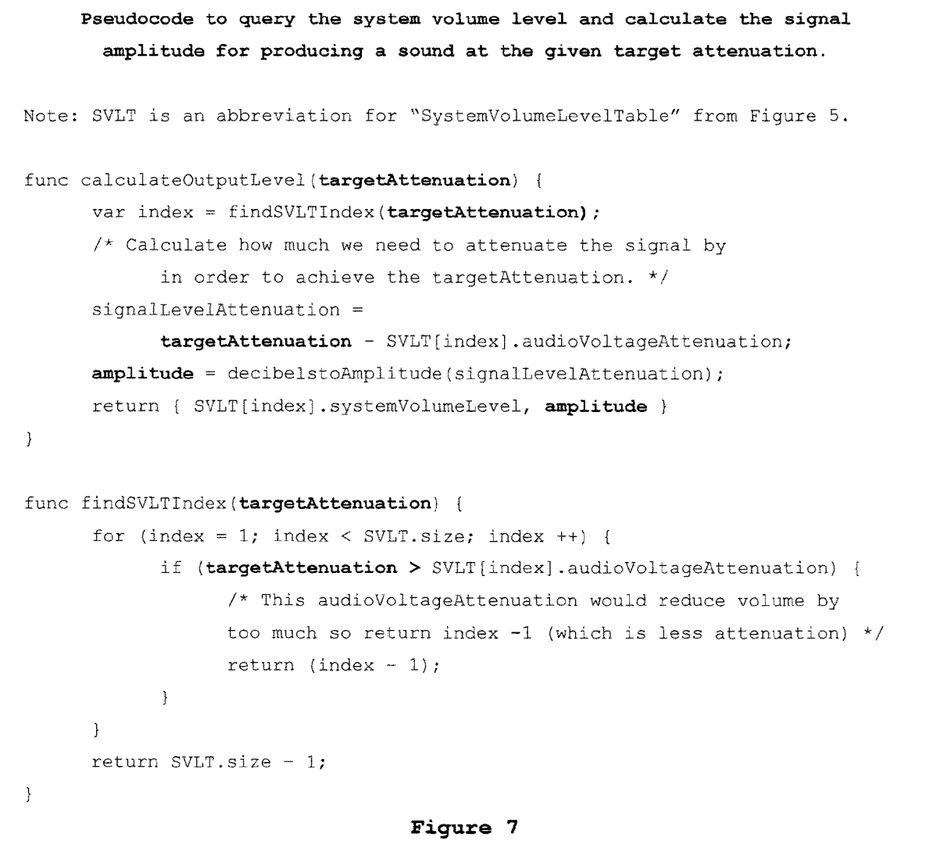
FIG. 7 shows pseudocode to find the required system volume level and signal amplitude for producing a sound at a given target attenuation.

Combining all of the above concepts, we can now describe an algorithm to find both the required system volume level and calculate the required signal amplitude for any requested target attenuation (see the pseudocode at FIG. 7).

Figure 8:
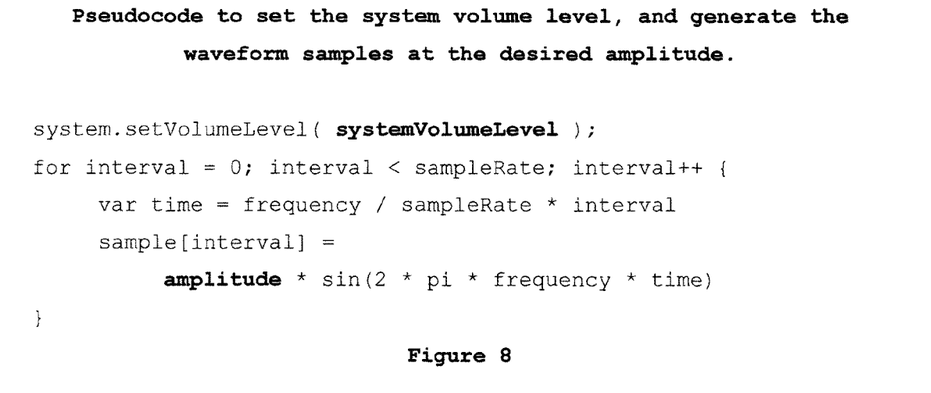
FIG. 8 shows pseudocode for generating the sound when given the output values of the code from FIG. 7.

The next step is to use the two values returned by the function shown at FIG. 7 (systemVolumeLevel and amplitude) to generate the sound. This is accomplished by simply filling an array with values that describe the sine wave using the amplitude that we have just calculated. See the pseudocode at FIG. 8. The "sample" array now contains the data required to pass to the sound generation module.

Headphone Calibration

For background information only, we will briefly describe how headphones calibration relates to the overall system described in this disclosure.

Recall that the system volume levels were measured electrically without a transducer attached, and that we described how to achieve any required attenuation by finding the right system volume level and the right signal amplitude. This lets us accurately attenuate from any maximum level.

However to use the SystemVolumeLevelTable to produce actual sound levels (dB SPL) we must know the maximum output of the attached headphone (db SPL). Measuring this value is called "calibration". In a typical implementation, the person skilled in the art would measure the maximum output ('maxSPL') of the left and right channels using a sound meter, and then store this value for each of the left and right channels for each unique pair of headphones. With this knowledge the target attenuation can be calculated by using the following formula:

targetAttenuation=targetSPL−maxSPL

Skilled persons will appreciate that other variants of this can be done, for instance, instead of calibrating by reading the maximum output of the transducer, it is very common to measure at a lower level of output, and then calculate the maximum output by assuming perfect linearity.

Other incarnations may not store the maxSPL, but instead use a globally defined best guess for maxSPL, and then only store an "adjustment" value from that maxSPL for each headphone.

Crosstalk Cancellation Method

With an understanding of the above-described sound-generation system, we can now describe how to compensate for crosstalk.

The following describes a system of compensating for predictable crosstalk. First we will show how to determine and store the correct values to use to generate a crosstalk compensation signal on the inactive channel. Then we will show how to use those stored values to generate a crosstalk signal. Finally, we will combine all of the concepts to show how to generate both the signal on the active channel and the crosstalk compensation signal on the inactive channel simultaneously.

Determining and Storing the Crosstalk Compensation Values

The first step is to measure how much crosstalk is present in the system. Using a sound meter, the crosstalk in the system is measured for each frequency at each desired attenuation level. (This is done for both the left and right channels).

The next step is to generate a signal on the inactive channel. Recall that we must only construct our crosstalk compensation signal by adjusting the amplitude and phase of the signal transmitted to the inactive channel since the system volume level is fixed at the value required by the active channel.

Figure 9:
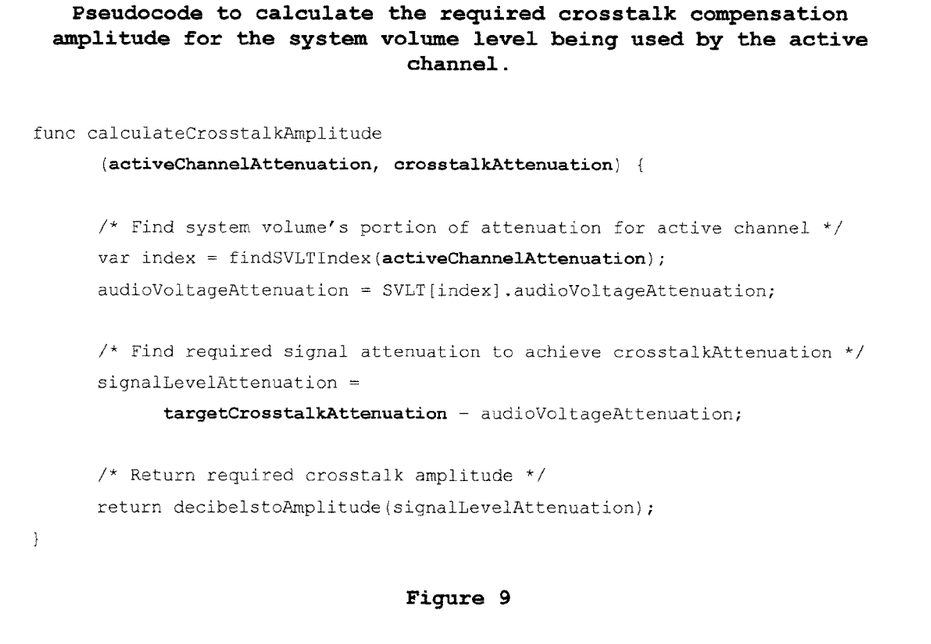
FIG. 9 shows pseudocode to calculate the required crosstalk compensation amplitude for the system volume level being used by the active channel.
Figure 10:
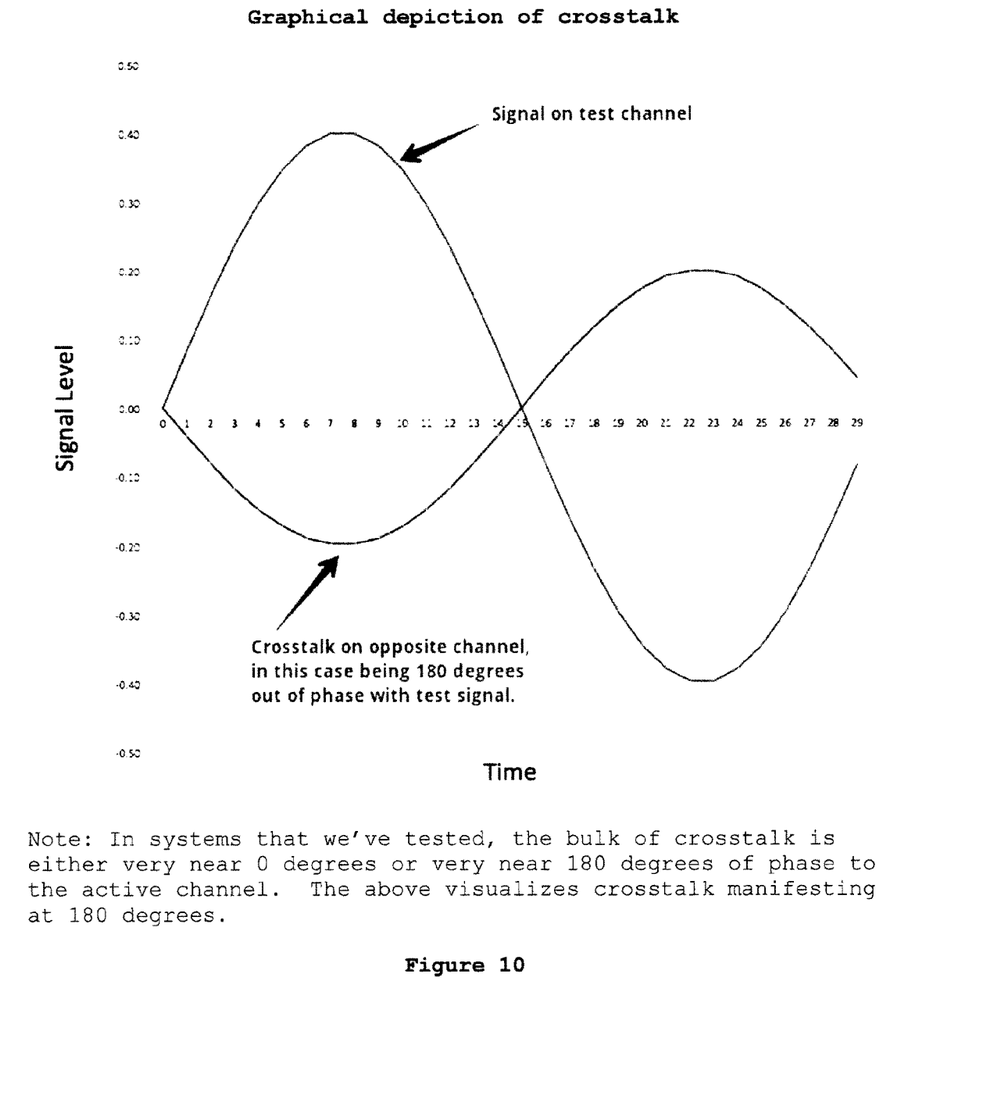
FIG. 10 is a graphical depiction of crosstalk.
Figure 12:
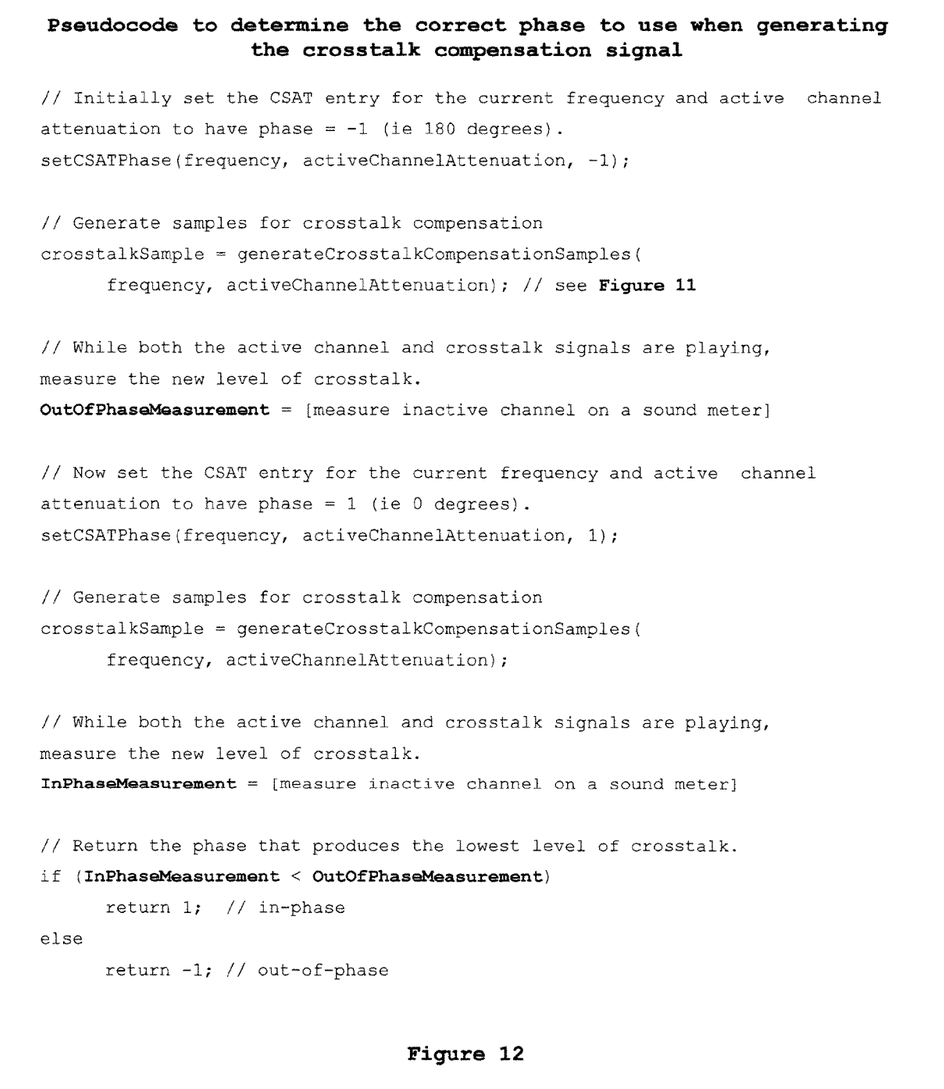
FIG. 12 shows pseudocode for determining the crosstalk signal and its phase.

We generate a signal at an initial amplitude (See pseudocode at FIG. 9) and choose either phase 0 or 180 degrees, and then re-measure to see how effective the signal is at reducing the crosstalk that is measured on the sound meter. The amplitude can also be iteratively adjusted further if required until the crosstalk is minimized. This is then repeated using a signal of the opposite phase. Of the two resulting candidate compensation signals (one at 0 degrees, and one at 180 degrees), the more effective signal is chosen and its amplitude and phase are recorded in a table. (See pseudocode at FIG. 12).

Figure 13:
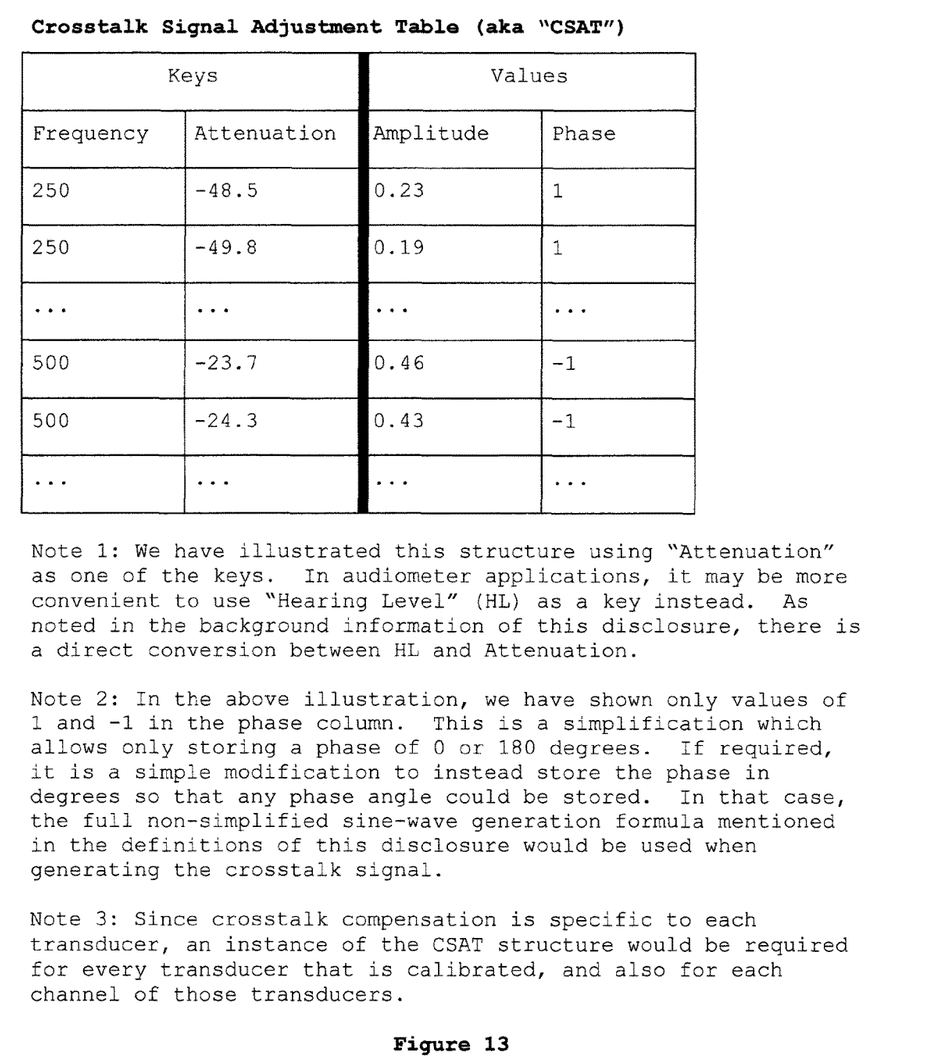
FIG. 13 is an example of a Crosstalk Signal Adjustment Table (aka "CSAT").

An example implementation of a table to store the crosstalk values in is shown in the Crosstalk Signal Adjustment Table (aka "LSAT") at FIG. 13.

Variations of this procedure can include testing phase angles other than 0 and 180 degrees, but the general methodology is the same.

Of note, for a given frequency, the crosstalk has been found to flip to the opposite phase at higher volumes as compared to the phase manifested at lower volumes. The level of crosstalk has also been found to vary in a non-linear fashion as volume increases. The solution described herein handles compensation of both non-linear and phase-inconsistent crosstalk in a system.

Crosstalk Signal Generation

Recall that we must only construct our crosstalk compensation signal by adjusting the amplitude of the signal transmitted to the inactive channel since the system volume level is fixed at the value required by the active channel.

To construct the require compensation signal, we populate an array of samples that will be sent to the operating system to generate the signal on the inactive channel.

Figure 11:
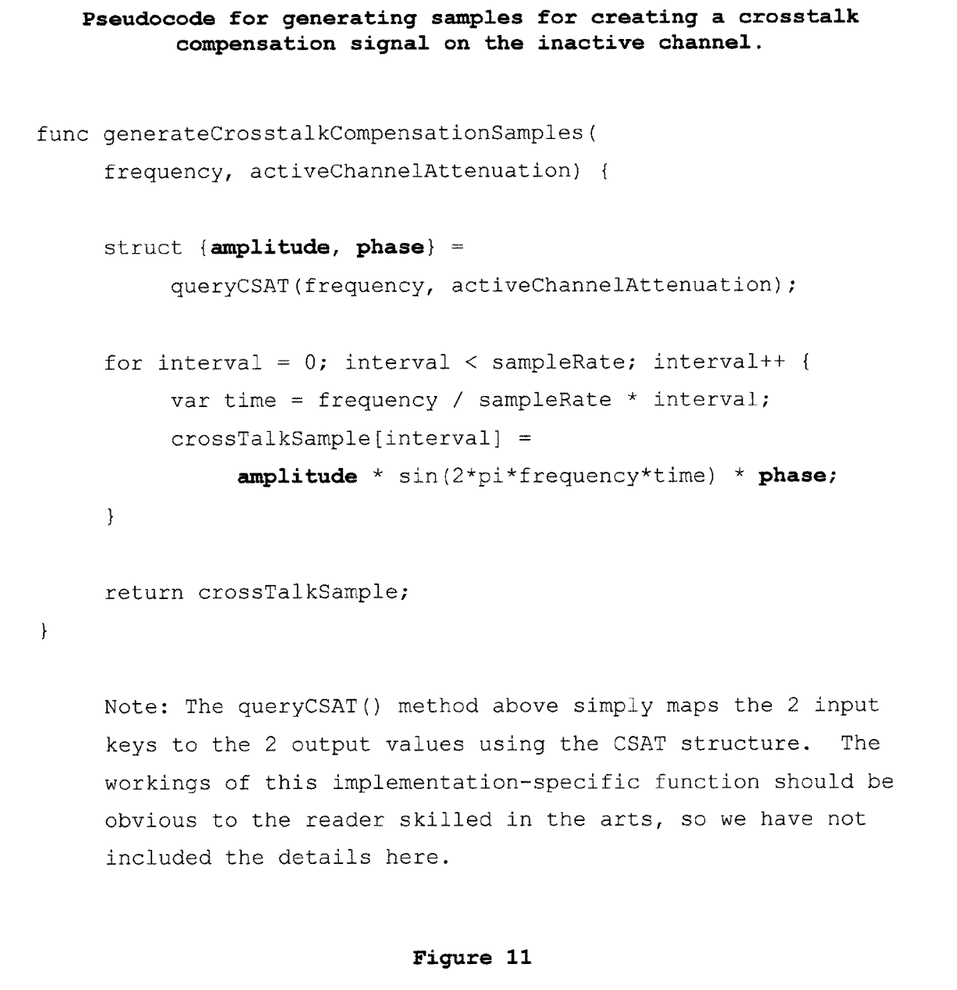
FIG. 11 shows pseudocode for generating samples for creating a crosstalk compensation signal on the inactive channel.

First we query the CSAT structure to find the amplitude and phase that is required to build the correct crosstalk compensation signal. Then we generate samples in exactly the same way as we do for the active channel. This is illustrated in the pseudocode at FIG. 11 while referencing the structure illustrated at FIG. 13.

Simultaneous Signal Generation on Active and Inactive Channels

Figure 14:
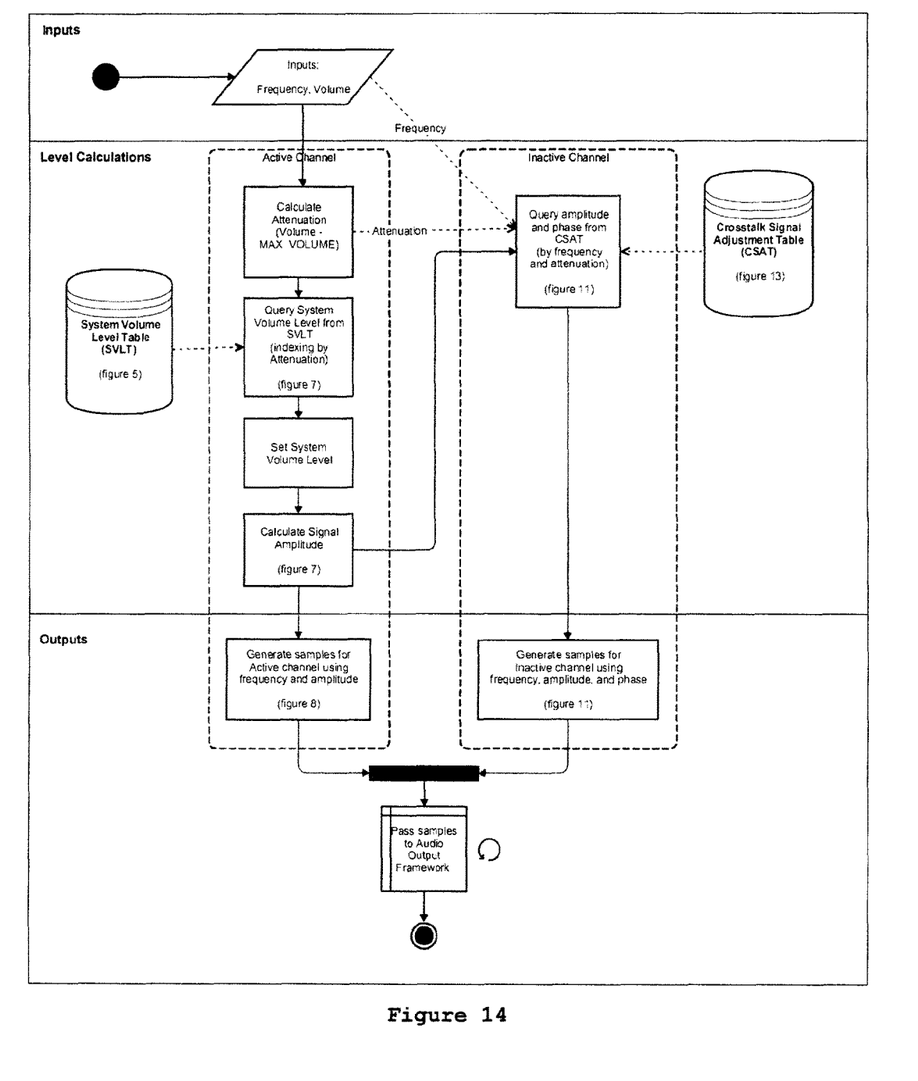
FIG. 14 shows a flowchart outlining the steps for producing a crosstalk cancellation signal.

The crosstalk signal must be generated simultaneously to the active channel's signal of course. The signal on the active channel and crosstalk cancellation signal should preferably be produced by the same code module which sends two channel samples to audio hardware, so that there is a high degree of accuracy to the time synchronization between the two channels. This is simply a matter of combining the concepts discussed above. The flowchart at FIG. 14 illustrates the steps required for producing both the active channel's signal and the crosstalk cancellation signal simultaneously. The chart can be divided into three sections: getting inputs, finding the required system volume and signal levels and finally producing the samples.

Although specific embodiments of the invention have been described, it will be apparent to one skilled in the art that variations and modifications to the embodiments may be made within the scope of the following claims.

We claim:

1. A computer-implemented method for reducing undesired crosstalk signals on an inactive channel of a device comprising the steps of:
    (i) determining system volume levels and associated signal amplitudes required to achieve a range of desired audio output attenuation levels on an active channel of the device;
    (ii) determining a crosstalk compensation signal comprising a signal amplitude and associated phase shift required to reduce undesired crosstalk on the inactive channel of the device for each desired audio output attention level in the range of desired audio output attenuation levels; and
    (iii) generating a desired audio output attenuation level on the active channel of the device by generating a signal at the determined system volume level and associated signal amplitude required to achieve said desired audio output attenuation level, and generating a contemporaneous crosstalk compensation signal on the inactive channel of the device by generating a signal at the determined signal amplitude and associated phase shift required to reduce the undesired crosstalk on the inactive channel.

2. The computer-implemented method of claim 1 wherein determining system volume levels and associated signal amplitudes required to achieve the range of desired audio output attenuation levels on the active channel of the device comprises the steps of:
    (i) measuring an output level at each system volume level of the device from maximum level to minimum level when the associated signal amplitude is set at 1;
    (ii) converting the output level at each such system volume level into decibels of attenuation;
    (iii) storing the decibels of attenuation for each system volume level in a database;
    (iv) querying the database to find the system volume level that attenuates the output level to as close to, but not more than, the desired audio output attenuation level;
    (v) calculating an attenuation required on the signal amplitude, which when added to the decibel of attenuation achieved at said system volume level, will result in producing the desired audio output attenuation level;
    (vi) storing the calculated attenuation required on the signal amplitude in the database; and
    (vii) repeating steps (iv) to (vi) for all system volume levels in the database.

3. The computer-implemented method of claim 2 wherein determining the crosstalk compensation signal comprising the signal amplitude and associated phase shift required to reduce undesired crosstalk on the inactive channel of the device for each desired audio output attention level in the range of desired audio output attenuation levels comprises the steps of:
    (i) generating a tone for the desired audio output attenuation level by controlling the system volume level and associated signal amplitude required to generate said tone;
    (ii) measuring the undesired crosstalk on the inactive channel of the device;
    (iii) calculating a signal amplitude that would be required to eliminate the undesired crosstalk on the inactive channel without modifying the system volume level;

(iv) generating a candidate crosstalk compensation signal at a phase of 180 degrees in accordance with step (iii);
(v) re-measuring the undesired crosstalk and iteratively adjusting the associated signal amplitude until the measured undesired crosstalk is minimized;
(vi) generating a candidate crosstalk compensation signal at a phase of 0 degrees in accordance with step (iii);
(vii) re-measuring the undesired crosstalk and iteratively adjusting the associated signal amplitude until the measured crosstalk is minimized; and
(viii) comparing the candidate crosstalk compensation signal at a phase of 180 degrees to the candidate crosstalk compensation signal at a phase of 0 degrees to determine which compensation signal is more effective at reducing the undesired crosstalk, and storing the signal amplitude and phase of such more effective crosstalk cancellation signal in a database.

4. The computer-implemented method of claim 2 wherein the device is a computer-based audiometer having channels that are not fully isolated.

5. The computer-implemented method of claim 3 wherein the step of generating the desired audio output attenuation level on the active channel of the device comprises querying the database for the system volume level and associated signal amplitude required to achieve said desired audio output attenuation level, and the step of generating a contemporaneous crosstalk compensation signal on the inactive channel of the device comprises querying the database for the signal amplitude and phase required to achieve said crosstalk compensation signal.

6. The computer-implemented method of claim 3 wherein the device is a computer-based audiometer having channels that are not fully isolated.

7. The computer-implemented method of claim 5 wherein the device is a computer-based audiometer having channels that are not fully isolated.

8. The computer-implemented method of claim 1 wherein the device is a computer-based audiometer having channels that are not fully isolated.

9. A computer program product comprising a computer readable memory storing computer executable instructions thereon that when executed by a computer with channels that are not fully isolated performs the method steps of claim 5.

10. A computer with channels that are not fully isolated that performs the computer-implemented method of claim 5 for reducing undesired crosstalk signals on an inactive channel of the computer.

11. A computer-based audiometer with channels that are not fully isolated that performs the computer-implemented method of claim 5 for reducing undesired crosstalk signals on an inactive channel of the computer-based audiometer.

12. A computer with channels that are not fully isolated that performs the computer-implemented method of claim 1 for reducing undesired crosstalk signals on an inactive channel of the computer.

13. A computer with channels that are not fully isolated that performs the computer-implemented method of claim 2 for reducing undesired crosstalk signals on an inactive channel of the computer.

14. A computer with channels that are not fully isolated that performs the computer-implemented method of claim 3 for reducing undesired crosstalk signals on an inactive channel of the computer.

15. A computer-based audiometer with channels that are not fully isolated that performs the computer-implemented method of claim 1 for reducing undesired crosstalk signals on an inactive channel of the computer-based audiometer.

16. A computer-based audiometer with channels that are not fully isolated that performs the computer-implemented method of claim 2 for reducing undesired crosstalk signals on an inactive channel of the computer-based audiometer.

17. A computer-based audiometer with channels that are not fully isolated that performs the computer-implemented method of claim 3 for reducing undesired crosstalk signals on an inactive channel of the computer-based audiometer.

18. A computer program product comprising a computer readable memory storing computer executable instructions thereon that when executed by a computer with channels that are not fully isolated performs the method steps of claim 1.

* * * * *